United States Patent [19]

Ferragamo

[11] Patent Number: 5,769,894
[45] Date of Patent: Jun. 23, 1998

[54] GRAFT ATTACHMENT DEVICE AND METHOD OF ATTACHMENT

[75] Inventor: Michael C. Ferragamo, N. Dighton, Mass.

[73] Assignee: Smith & Nephew, Inc., Memphis, Tenn.

[21] Appl. No.: 795,947

[22] Filed: Feb. 5, 1997

[51] Int. Cl.⁶ .................................................. A61F 2/08
[52] U.S. Cl. .............................. 623/13; 606/72; 606/148; 606/232
[58] Field of Search .................. 623/13, 16; 606/72, 606/148, 232

[56] References Cited

U.S. PATENT DOCUMENTS

5,139,520  8/1992  Rosenberg ................................. 623/13
5,306,301  4/1994  Graf et al. ................................. 623/13
5,645,588  7/1997  Graf et al. ................................. 623/13

Primary Examiner—Randy C. Shay
Attorney, Agent, or Firm—Fish & Richardson P.C.

[57] ABSTRACT

A tissue graft is secured within a bone passage by providing a graft fixation member sized to pass through the bone passage, attaching a suture having a pair of free ends to the tissue graft and tying the suture to the fixation member so that the free ends pass through an opening in the fixation device from a first side to a second side and a length of the suture extends between the tissue graft and fixation member. The length of the suture between the tissue graft and the fixation member is adjusted by pulling at least one of the free ends, and the suture is secured to the fixation member to maintain the adjusted length.

14 Claims, 5 Drawing Sheets

GRAFT ATTACHMENT DEVICE AND METHOD OF ATTACHMENT

BACKGROUND OF THE INVENTION

This invention relates to anchoring tissue grafts.

An increasing number of surgical techniques are now performed arthroscopically. One type of arthroscopic procedure reconstructs the anterior cruciate ligament (ACL) in the knee. Several ACL reconstruction techniques are described in U.S. Pat. No. 5,139,520, issued to Rosenberg (hereafter, the "Rosenberg '520 patent"), which is incorporated herein by reference.

When the ACL has ruptured and is nonrepairable, it is usually replaced in the knee using a substitute graft harvested from the patient or from a donor. For example, the substitute ACL graft may be selected, according to surgeon preference, from a portion of a patellar tendon having a bone block or plug at each end. Alternatively, artificial grafts formed synthetically or with a combination of artificial and natural material, such as a ligament augmentation device (LAD) to which tissue is sutured, may be used as a substitute graft. The term "graft" is used herein to encompass all of these tissue replacement items.

In general, the replacement graft is implanted by securing one end of the graft in a socket formed in a femoral channel or passage formed within the femur with the other end of the graft passing through a tibial channel and secured to the tibia adjacent the tibial channel. Generally, graft sutures are used to affix each end of the graft to a fastener (e.g., an interference screw or a post) which is then secured to the bone. Descriptions of these fasteners and methods of forming the passages through the tibia and femur are described in greater detail in the Rosenberg '520 patent.

In another approach for affixing a graft suture, described in U.S. Pat. No. 5,306,301, issued to Graf (hereafter, the "Graf '301 patent"), and incorporated herein by reference, the ends of graft suture are secured at the femoral cortex using a fixation button. The fixation button has an elongated shape and a pair of openings through which the suture is passed and then tied off. In this approach, the surgeon, prior to the implantation procedure, measures the total length of the femoral channel and the length of the socket portion within which the bone block of the graft is to be implanted. These measurements are used to predetermine the required length of the graft suture (called the "suture span") needed to extend from the end of the properly seated bone block and the femoral cortex. The surgeon then ties the graft suture to the openings formed in the fixation button to provide the predetermined desired suture span. The fixation button and replacement graft are then passed through the tibial and femoral channels until the graft is properly seated within the socket portion of the femoral passage and the fixation button is firmly seated against the femoral cortex. The tissue graft is then tensioned and anchored at its opposite end using a fixation screw secured within the tibia.

SUMMARY OF THE INVENTION

The invention features attaching suture secured to a tissue graft to a graft fixation member that is configured to allow the length of the suture between the fixation member and tissue graft to be adjusted, and to maintain the adjusted length when the suture is secured to the graft fixation member.

In a general aspect of the invention, a method of securing a tissue graft within the bone passage includes providing a graft fixation member which is sized to pass through the bone passage, attaching suture having a pair of free ends to the tissue graft, tying the suture to the fixation member by passing the free ends through the opening from the first side to the second side of the fixation member, wrapping the free ends around a portion of the fixation member by passing the free ends from the second side to the first side and passing the free ends back from the first side to the second side, a length of the suture extends between the tissue graft and fixation member, adjusting the length of the suture by pulling at least one of the free ends, and securing the suture to the portion of the fixation member to maintain the suture extending between the tissue graft and fixation member at the adjusted length.

Among other advantages, this method allows the suture to be easily pulled through the fixation member to adjust the suture length, and then cinched and locked (e.g., by tying the suture to the fixation member) into place when the desired length between the fixation member and tissue graft has been achieved. Thus, the tissue graft can be properly positioned within the bone passage without any need for pre-measuring the length of the suture which extends between the tissue graft and the fixation member at the surface of the bone adjacent the passage. Moreover, adjusting the length of the suture can be performed quickly and easily to reliably secure the tissue graft within the bone passage.

Embodiments of this aspect of the invention may include the following features.

Adjusting the length of the suture can be performed either before or after passing the fixation member through the passage. The graft fixation member includes multiple openings for implementing various tying arrangements of the suture to the fixation member. For example, with a second opening formed in the fixation member, tying the suture to the fixation member includes passing the free ends through the first opening from the first side to the second side, wrapping the free ends around a portion of the fixation member by passing the free ends from the second side to the first side and passing the free ends through the second opening from the first side to the second side of the fixation member. An alternative tying arrangement includes passing the suture free ends through the first opening from the first side to the second side, wrapping the free ends around a portion of the fixation member by passing the free ends through the second opening from the second side to the first side and passing the free ends through the first opening from the first side to the second side of the fixation member passing the free ends through the second opening from the second side to the first side, and then passing the free ends back through the first opening from the first side to the second side (for the second time). In either case, passing the free ends of the suture back through the second opening forms a closed loop around a portion of the fixation member with a portion of the suture crossing by and contacting another portion of the suture to form a hitch-like interference lock fit.

A third opening, positioned between the first opening and the second opening, can also be provided in the fixation member. The third opening is preferably larger than the first and second openings to facilitate adjusting the suture length. With this arrangement, tying the suture to the fixation member includes passing the suture free ends through the first opening from the first side to the second side, passing the free ends over the third opening and through the second opening from the second side to the first side, and then wrapping the suture around a portion of the body between the second and third openings by passing the free ends through the third opening from the first side to the second side. A rib-like portion of the body between the first-mentioned opening and second opening is disposed substantially halfway along the elongated length of the body. The third opening and position of the rib-like portion provides the same interference lock fit as described above, but in a more balanced way relative to the length of the fixation member. That is, when the fixation member is in contact with the bone, tension at the fixation member by the suture attached to the tissue graft is distributed through the fixation member more evenly to the bone surfaces adjacent the passage. Moreover, the size and the positions of the openings with respect to each other allow the suture to pass smoothly through the openings during adjustment of the length.

In one embodiment, the length of the suture extending between the tissue graft and the graft fixation member is adjusted after passing the fixation member through the bone passage to place the tissue graft in tension. Alternatively, when the desired length of the suture connecting the tissue graft and graft fixation member is known, the length can be adjusted prior to passing the fixation member through the passage.

The length of suture extending between the tissue graft and the graft fixation member forms a loop or a sling which is attached to the tissue graft.

In another aspect of the invention, a device for securing a tissue graft within a passage in a bone includes a member having first and second sides, an opening extending between the first and second sides, and a suture-wrap portion, the member being elongated in a first dimension that extends between first and second ends of the member and a second dimension transverse to the first dimension, the member being configured so that: (1) the second dimension is smaller than a diameter of the bone passage to allow the member to be passed through the bone passage when the first dimension is oriented along the passage, and (2) the first dimension is larger than the diameter of the bone passage so that after the member is passed through the passage and oriented with the first dimension transverse to the passage, the first surface of the first and second ends of the member engage surfaces of the bone adjacent to the passage; suture attached to the tissue graft and having free ends; the suture-wrap portion and the opening being configured to allow the suture to be tied to the member such that the free ends of the suture are received through the opening from the first side to the second side of the member, wrapped around the suture-wrap portion from the second side to the first side and passed back from the first side to the second side of the member so that an intermediate portion of the suture extending between the member and the tissue graft can be adjusted to a desired length by pulling at least one of the free ends, and the desired length of the intermediate portion thereafter maintained by securing the suture to the suture-wrap portion.

Embodiments of this aspect may include one or more of the following features.

The member is configured to have a dimension (e.g., the width) which allows the member to be passed through the bone passage and another dimension (e.g., the length) larger than the diameter of the bone passage so that after the member is passed through the passage and rotated or "flipped", ends of the member engage surfaces of the bone adjacent to the passage.

The member includes multiple openings for tying the suture to the member in any of the arrangements described above. In general, the openings are sized and shaped in relation to the width and thickness of the particular suture used to secure the implanted tissue graft within the bone passage. Specifically, the first and second openings are sized so that the suture passes easily therethrough with the third opening sized to be larger than the first and second openings to provide the hitch-like interference locking fit described above. The larger opening is sized to facilitate the length adjustment and to prevent the suture from slipping from the member when the intermediate portion is locked at its desired length. The openings are preferably formed with a circular shape with rounded inner edges to avoid chafing or cutting of the suture. One of the openings receives a releasably threaded filament adapted to draw the member through the passage. Alternatively, the releasably threaded filament is received within a separate opening formed within the member.

Other features and advantages will become apparent from the following detailed description, and from the claims.

DESCRIPTION OF PREFERRED EMBODIMENTS

Figure 1:
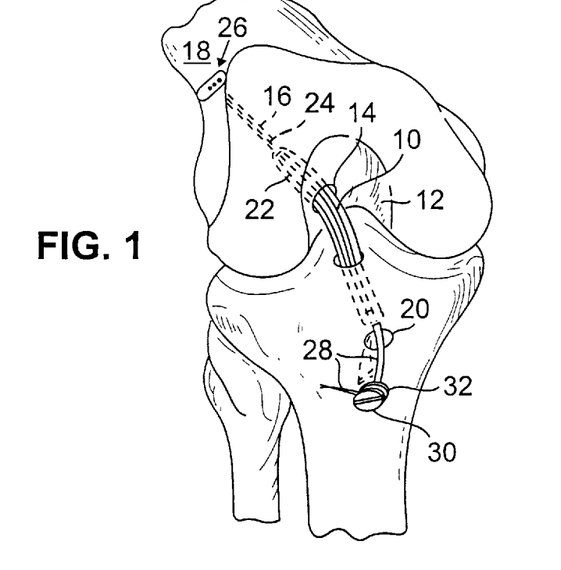
FIG. 1 shows a knee joint in which a graft fixation member is used.

Referring to FIG. 1, a knee joint is shown in which a tissue graft 10 (e.g., a patellar tendon graft) is being implanted in an anterior cruciate ligament (ACL) repair and reconstruction procedure. Prior to implanting tissue graft 10, a notchplasty procedure is preferably performed to expand the intercondylar notch 12 of the femur bone. A notchplasty procedure is described in detail in the Rosenberg '520 patent. A femoral channel 14 for receiving one end of tissue graft 10 is then drilled from notch 12 a predetermined distance within the femur with a passing channel 16 of reduced diameter drilled further through the femur from femoral channel 14 to a region of femoral cortex 18. A tibial channel 20 for receiving the other end of tissue graft 10 is drilled from an anterior region of the tibia to a region near the opening of femoral channel 14. The procedure for providing the femoral channel 14, passing channel 16 and tibial channel 20 is described in greater detail in Graf '301 patent.

One end of tissue graft 10 includes a bone block 22 which is shaped and sized in close conformity with femoral channel 14 to ensure optimal healing. A length of suture 24 has one end attached to bone block 22 and the other end secured at femoral cortex region 18 with a graft fixation member 26 which will be described in greater detail below. The distal end of tissue graft 10 includes a second length of suture 28 which is attached to the tibia with a fixation screw 30 about 1.5 cm below the entrance to tibial channel 20. A washer 32 either attached to or positioned under the head of fixation screw 30 helps in holding the suture in place when screw 30 is tightened.

Figure 2:
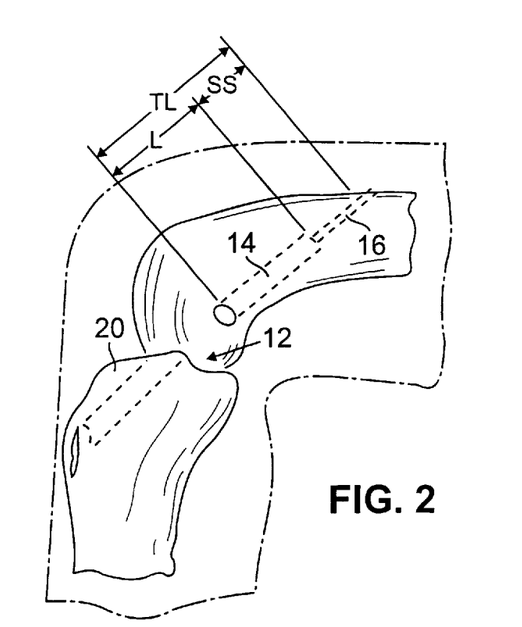
FIG. 2 is another view of the knee joint of FIG. 1.

Referring to FIG. 2, length (L) of femoral channel 14 is selected by the surgeon in accordance with the length of bone block 22 and the desired insertion distance of tissue graft 10 within the femur. The span of suture 24, designated as SS, is approximately that of passing channel 16 so that the sum of the desired insertion length (L) and span of suture (SS) is the measured total length (TL) from the opening of femoral channel 14 to the opening at femoral cortex 18. Each of these dimensions is measured prior to implanting the tissue graft so that during the implantation procedure, the surgeon, under arthroscopic observation, can be assured that tissue graft 10 has been properly positioned within femoral channel 14.

Figure 3:
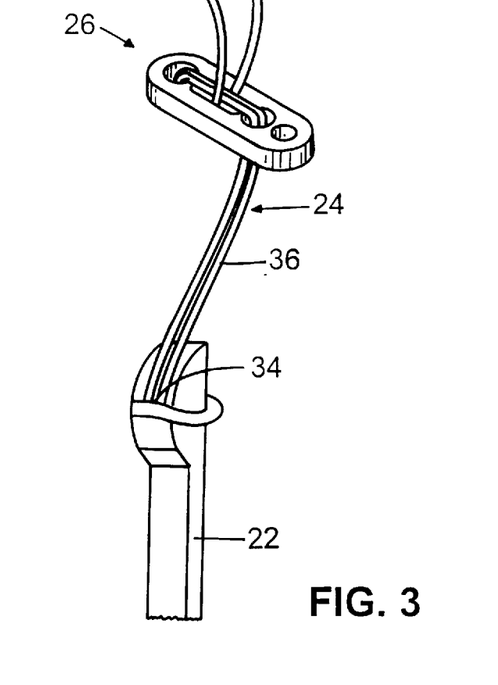
FIG. 3 illustrates the graft fixation member attached to a tendon bone plug.

Referring to FIG. 3, graft fixation member 26 and the manner in which it is attached to bone block 22 and suture 24 is shown. Suture 24, which is for example a polyester closure tape (e.g., Merselene, a product of Ethicon Inc., Cincinnati, Ohio) is threaded through a pre-drilled hole 34 within bone block 22 to form a suture loop 36 extending between fixation member 26 and bone block 22. As will be described in greater detail below, fixation member 26 is configured to allow the length of loop 36 to be easily adjusted to secure tissue graft 10 within femoral channel 14.

Figure 4:
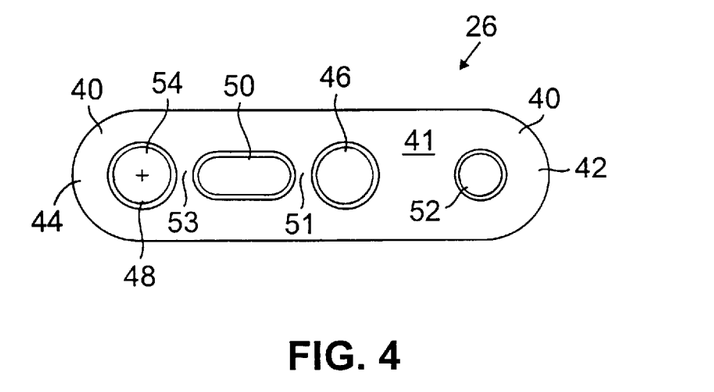
FIG. 4 is a plan view of the graft fixation member of FIG. 1.

Referring to FIG. 4, fixation member 26 includes an elongated body 40 formed of a biocompatible material (e.g., Delrin® polymer) and having a length of about 0.55 inches, a width of about 0.16 inches and a thickness of about 60 mils. Elongated body 40 has a width which allows fixation member 26 to be pulled through tibial channel 20 and femoral channel 14. Elongated body 40 has flat upper and lower surfaces 41, 43, and a rounded leading end 42 and a rounded trailing end 44. A series of suture openings 46, 48, 50 and a lead hole 52 extend through body 40 from upper surface 41 to lower surface 43. Suture openings 46, 48 are circular and have diameters (d) of about 0.078 inches. Diameter (d) is selected primarily in accordance with the width and thickness of suture tape 24 so that tape 24 can pass easily through openings 46, 48. Suture opening 48 has a center 54 spaced from the edge of rounded end 44 a distance approximately equal to the diameters of openings 46, 48.

Elongated suture opening 50 is formed between suture openings 46, 48 and is separated therefrom by ribs 51, 53, respectively, both of which have a width of about 0.020 inches. For reasons which are discussed in greater detail below, rib 51 is centered substantially along the length of elongated body 40. Elongated suture opening 50 has an oblong shape longer and thinner than suture openings 46, 48. In particular, elongated suture opening 50 has long and short dimensions of about 0.117 and 0.062 inches, respectively. Openings 46, 48, 50 and hole 52 have rounded inner edges to avoid chafing of suture 24, 59.

Hole 52 which is smaller than suture openings 46, 48 and elongated suture opening 50 is formed at rounded leading end 42 and is used to carry a leading suture 59 (FIG. 7) for pulling fixation member 26 through femoral passage 14 and passing passage 16.

Referring to FIGS. 5A–5C and FIG. 6, suture 24 is threaded through suture openings 46, 48 and elongated suture opening 50 of fixation member 26 as follows. Free ends 58a, 58b of suture loop 36 are passed up through suture opening 46 from lower surface 43 to upper surface 41 (FIG. 5A) so that suture loop 36 is slightly longer than the measured length SS described above (FIG. 2).

Figure 5A:
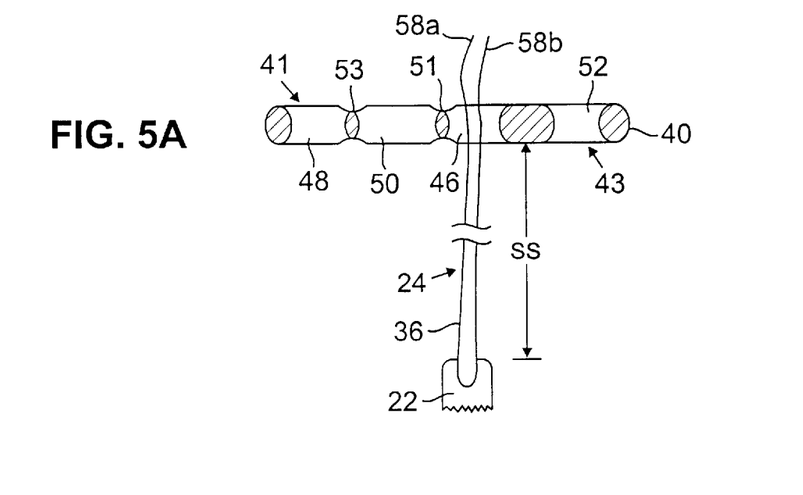
FIGS. 5A–5C are cross-sectional side views of the graft fixation member of FIG. 4 at different stages of threading a suture therethrough.
Figure 5B:
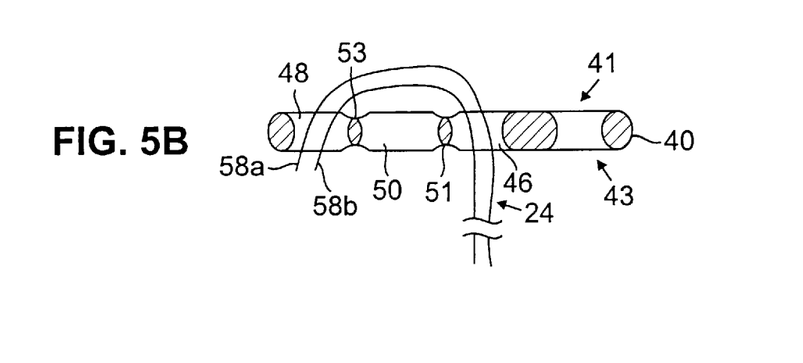
Figure 5C:
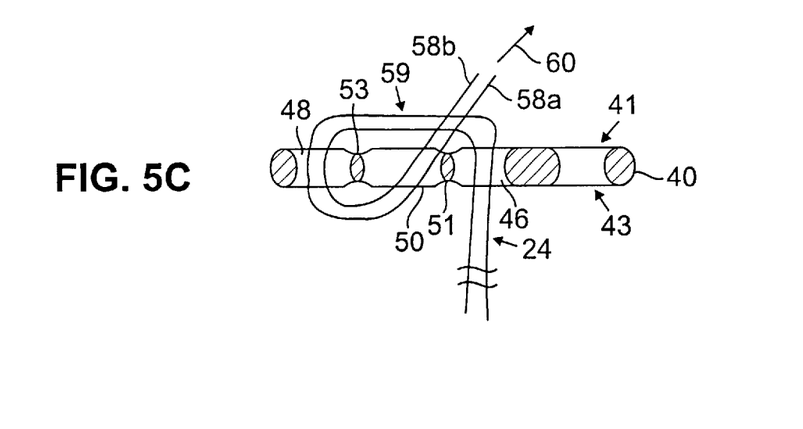
Figure 6:
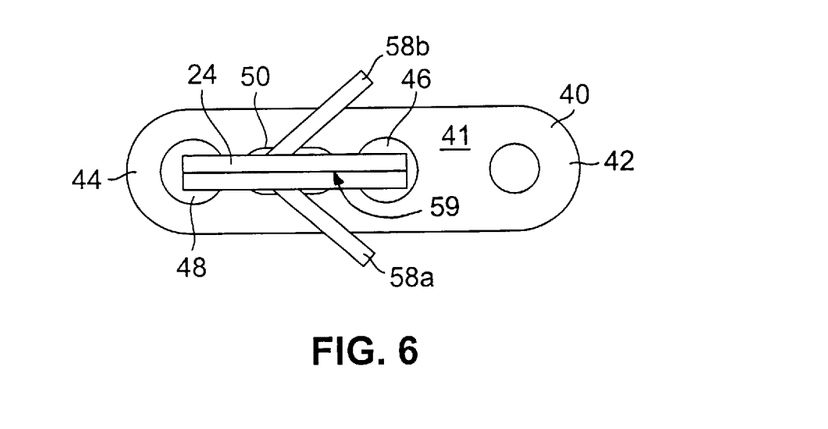
FIG. 6 is a plan view of the graft fixation member of FIG. 5C with the suture threaded therethrough.

Free ends 58a, 58b are passed over elongated suture opening 50 and then threaded from upper surface 41 to lower surface 43 of fixation member 26 down through suture opening 48 (FIG. 5B). Free ends 58a, 58b are then looped around rib 53 by passing them through elongated suture opening 50 from lower surface 43 to upper surface 41 (FIG. 5C) with free ends 58a, 58b being threaded on opposite sides of a portion 59 of suture 24 that lies over elongated suture opening 50 at upper surface 41 (FIG. 6).

Prior to the implantation procedure, the length of loop 36 is selected to be slightly longer than suture span SS so that fixation member 26 is assured of extending beyond femoral cortex 18 when tissue graft 10 is properly seated within femoral passage 14. To increase the initial length of loop 36, portion 59 of suture 24 extending over upper surface 62 is lifted to loosen suture 24 from graft fixation member 26, and loop 36 is pulled to draw suture 24 back through suture openings 46, 48 and elongated opening 50, thereby increasing the length of loop 36. In its loosened condition, suture 24 is allowed to pass easily through suture openings 46, 48 and elongated opening 50. It is only when the suture ends 58a, 58b are pulled to tighten suture 24 around ribs 51, 53 will an interference locking fit be formed, thereby cinching and securing loop 36 at the desired length. Frictional contact between a section of suture 24 which is being passed from lower surface 43 to upper surface 41 through elongated opening 50 and the portion 59 of suture 24 which overlies elongated opening 50 provides the interference locking fit, thereby preventing suture 24 from slipping back through elongated opening 50 and suture support openings 46, 48.

Figure 7:
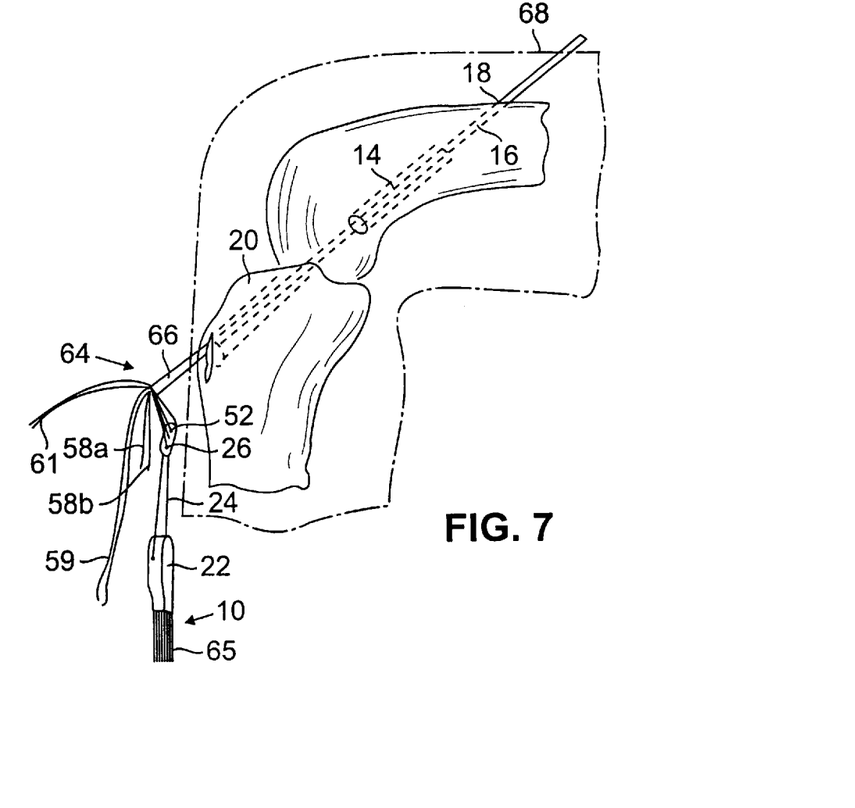
FIG. 7 illustrates insertion of the graft fixture member, the suture, the graft and bone plug into the bone passage.
Figure 8:
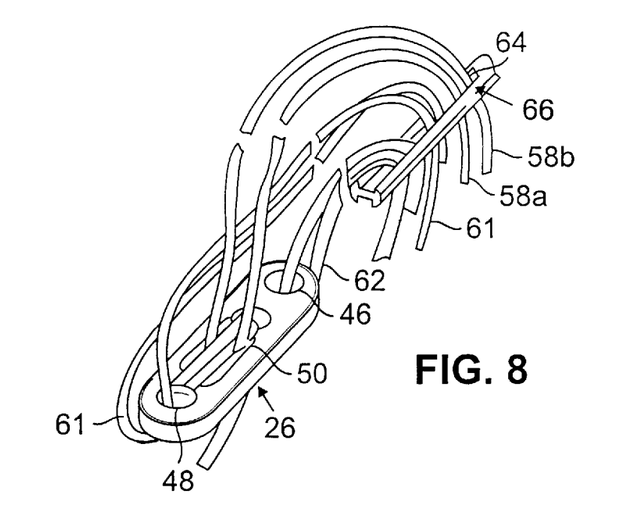
FIG. 8 shows an enlarged view of the distal end of the passing pin prior to insertion of the graft fixture member, the suture, the graft and bone plug into the bone passage.

The procedure for placing graft fixation member 26 in the position shown in FIG. 1 follows. Drilling procedures are performed to provide an appropriately sized tibial channel 20 extending through the tibia and femoral passage 14 in the manner described in the Graf '301 patent. Suture loop 36 is adjusted to be approximately that of and slightly longer than suture span SS. However, suture 24 is threaded loosely through suture openings 46, 48 and elongated opening 50 so that loop 36 is not cinched. Referring to FIGS. 7 and 8, a leading suture 62 is threaded through hole 52 of fixture member 26 and then through a slot 64 of a passing pin 66. A trailing suture 61 is threaded through hole 48, and along with free ends 58a, 58b is also threaded through slot 64 of passing pin 66. It is preferable that sutures 61, 62 be perceptively different from each other, such as by having different diameters; for example, No. 5 Ticron for lead suture 62 and No. 2 Ticron for trailing suture 61. Alternatively, different color filaments can be used. Passing pin 66 is then inserted through an incision below the knee, and advanced through tibial channel 20, femoral channel 14, passing channel 16, the quadricep tissue, and skin 68 of the thigh. Free ends 58a, 58b and leading suture 59 are withdrawn beyond skin 68 using passing pin 66.

The surgeon then pulls leading suture 59 until fixation member 26 emerges from passing channel 16 at femoral cortex 18. The surgeon then pulls on trailing suture 61 so that fixation member 26 flips from a length-wise orientation to a width-wise orientation so that fixation member 26 straddles the opening of channel 16 with rounded ends 42, 44 moving into contact against femoral cortex 18. In this position, rib 51, around which suture loop 36 is wrapped, is centered substantially over the center of the opening of channel 16 so that, after cinching the interference knot, tension from the suture (when the tissue graft is in its final position) is distributed through the fixation member more evenly to the bone surfaces adjacent the passage.

Tissue graft 10 includes a marker 65, previously placed on the graft, which is viewed arthroscopically and when aligned with the opening of femoral channel 14 at intercondylar notch 12 indicates that graft 10 is properly positioned within channel 14. At this point, filament ends 58a, 58b are pulled together in a direction away from fixation member 26 (in the direction of arrow 60 in FIG. 5C) to shorten the length of loop 36 and fixation member 26 is firmly seated against the femoral cortex. While the surgeon continues to examine marker 65 to ensure that it does not move, one or both of free ends 58a, 58b is further pulled to cinch the interference knot, thereby maintaining the length of loop 36 at is adjusted length. One or both suture ends 58a, 58b are then pulled further to cinch and provide the interference lock fit needed to maintain the length of loop 36 at is adjusted length. Because less force is required to tighten or firm-up the interference knot, the surgeon need only pull one of filament ends 58a, 58b to tighten the knot. Tissue graft 10 is then tensioned and anchored at its opposite end using fixation screw 30 (FIG. 1) secured within the tibia. Finally, free ends 58a, 58b are tied off at fixation member 26 to eliminate any chance of the interference knot slipping.

Other embodiments are within the scope of the claims.

For example, an alternative approach for securing a tissue graft within a bone passage using fixation member 26 is available. Specifically, rather than approximating the desired length of suture loop 36 and adjusting its length prior to cinching the interference knot, the surgeon can precisely measure the desired length using, for example, the approach described in the Graf '301 patent. The surgeon can then cinch the interference knot prior to passing tissue graft 10 with fixation member 26 through the tibial channel 20 and femoral channel 14.

Although the tissue graft described above in conjunction with FIGS. 1–7 is one having a bone block, other types of grafts may be attached to graft fixation member to including ligament augmentation devices (LAD) formed of artificial ligament material to which the tissue is sutured.

In general, graft fixation member 26 can be used to secure any suitable kind of grafts, such as alografts, autografts, and xenografts and can be used in surgical soft tissue reconstruction procedures other than those related to ACL reconstruction.

Moreover, the use of graft fixation member 26 can also be used to secure tissue graft 10 at the tibia in place of fixation screw 30.

In certain surgical procedures, the size of the diameter of the bone passage may be limited. In such procedures, the length of fixation member 26 may be reduced by eliminating leading hole 36 which receives leading suture 58 for pulling the fixation member through the bone passage. Thus, the overall length of fixation member 26 can be reduced with a leading suture threaded through the opening closest to the leading rounded end 32 of fixation member, such as opening 46. In other applications, openings 46, 48 and 50 may have other polygonal shapes, including a rectangular shape.

Figure 9:
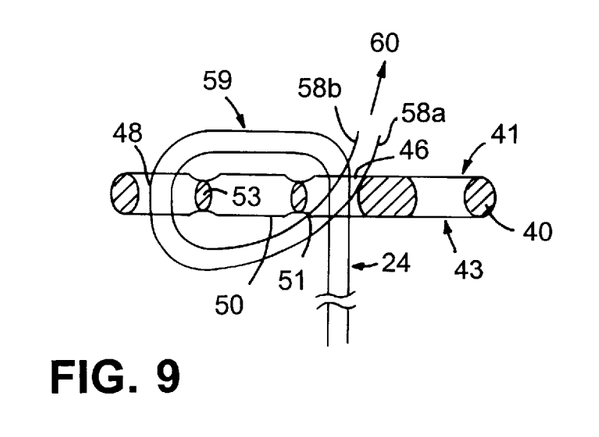
FIG. 9 is a cross-sectional side view of the graft fixation member of FIG. 4 showing an alternative approach for threading a suture therethrough.

Referring to FIG. 9, in an alternative suture threading approach, after free ends 58a, 58b of suture loop 36 are passed up through suture opening 46 from lower surface 43 to upper surface 41, free ends 58a, 58b are passed over elongated suture opening 50 and then threaded from upper surface 41 to lower surface and down through suture opening 48. Free ends 58a, 58b are then looped around ribs 53, 51 and passed through suture opening 46 from lower surface 43 to upper surface 41 with free ends 58a, 58b being threaded on opposite sides of a portion 59 of suture 24 at upper surface 41.

What is claimed is:

1. A method of securing a tissue graft within a bone passage comprising the steps of:

providing a graft fixation member having an opening extending between a first side and a second side of the fixation member and being sized to pass through the bone passage such that the first side engages the bone adjacent to the passage after said member has been passed through the passage;

attaching a suture having a pair of free ends to the tissue graft;

tying the suture to the fixation member by passing the free ends through the opening from the first side to the second side of the fixation member, wrapping the free ends around a portion of the fixation member by passing the free ends from the second side to the first side and passing the free ends back from the first side to the second side, a length of the suture extending between the tissue graft and the fixation member;

adjusting the length of the suture by pulling at least one of the free ends; and securing the suture to the portion of the fixation member to maintain the suture extending between the tissue graft and the fixation member at the adjusted length.

2. The method of claim 1 further comprising the step of passing the fixation member through the passage before performing the adjusting step.

3. The method of claim 1 further comprising the step of passing the fixation member through the passage after performing the adjusting step.

4. The method of claim 1 wherein the graft fixation member includes a second opening extending between the first and second sides, and the step of tying the suture to the fixation member includes, after passing the free ends through the first-mentioned opening, wrapping the free ends around a portion of the fixation member by passing the free ends from the second side to the first side and passing the free ends through the second opening from the first side to the second side.

5. The method of claim 1 wherein the graft fixation member includes a second opening extending between the first and second sides, and the step of tying the suture to the fixation member includes:

after passing the free ends through the first-mentioned opening, wrapping the free ends around a portion of the fixation member by passing the free ends through the second opening from the second side to the first side; and passing the free ends through the first opening from the first side to the second side.

6. The method of claim 5 further comprising releasably threading a filament through one of the openings to draw the fixation member through the bone passage.

7. The method of claim 1 further comprising forming the length of suture extending between the fixation member and the tissue graft as a loop, the adjusting step including adjusting the length of the loop.

8. The method of claim 1 wherein the graft fixation member has a length and includes a second opening extending between the first and second sides of the fixation member and a third opening, disposed between the first-mentioned opening and the second opening and extending between the first and second sides of the fixation member, and the step of tying the suture to the fixation member includes:

after passing the free ends through the first-mentioned opening, passing the free ends over the third opening and through the second opening from the second side to the first side; and wrapping the suture around a portion of the fixation member between the second and third openings by passing the free ends through the third opening from the first side to the second side.

9. The method of claim 8 further comprising providing the third opening to be larger than the first-mentioned and second openings, the portion of the fixation member between the first-mentioned opening and the third opening disposed substantially halfway along the length of the fixation member.

10. The method of claim 8 wherein the fixation member includes a fourth opening at an end region of the fixation member and extending between the first and second sides of said fixation member, and further comprising threading a filament adapted to draw the fixation member through the bone passage through said fourth opening.

11. A device in combination with a tissue graft for securing the tissue graft within a passage in a bone comprising:

a member having first and second sides, an opening extending between the first and second sides, and a suture-wrap portion, the member being elongated in a first dimension defining a length that extends between first and second ends of the member, the member having a second dimension transverse to the first dimension, the member being configured so that: (1) the second dimension is smaller than a diameter of the bone passage to allow the member to be passed through the bone passage when the first dimension is oriented along She passage, and (2) the first dimension is larger than the diameter of the bone passage so that after the member is passed through the passage and oriented with the first dimension transverse to the passage, the first side of the first and second ends of the member engage surfaces of the bone adjacent to the passage;

suture attached to the tissue graft and having free ends;

the suture-wrap portion and the opening being configured so that the suture is tied to the member with the free ends of the suture received through the opening from the first side to the second side of the member, wrapped around the suture-wrap portion from the second side to the first side and passed back from the first side to the second side of the member so that an intermediate portion of the suture extending between the member and the tissue graft can be adjusted to a desired length by pulling at least one of the free ends, and the desired length of the intermediate portion thereafter maintained by securing the suture to said suture-wrap portion.

12. The device of claim 11 further comprising a second opening larger than the first-mentioned opening, a portion of the member between the first-mentioned opening and second opening disposed substantially halfway along the length of the member.

13. The device of claim 12 wherein the openings are circular.

14. The device of claim 11 wherein the member further comprises a hole configured to receive a releasably threaded filament for drawing the member through the bone passage.

* * * * *